US012605543B2

(12) United States Patent
Weiss et al.

(10) Patent No.: US 12,605,543 B2
(45) Date of Patent: Apr. 21, 2026

(54) MRI INDUCED NERVE STIMULATION AS MEANS FOR COMMUNICATION WITH PATIENT

(71) Applicant: KONINKLIJKE PHILIPS N.V., Eindhoven (NL)

(72) Inventors: Steffen Weiss, Hamburg (DE); Mark Thomas Johnson, Arendonk (BE); Gereon Vogtmeier, Aachen (DE); Christoph Günther Leussler, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 651 days.

(21) Appl. No.: 18/008,195

(22) PCT Filed: Jun. 10, 2021

(86) PCT No.: PCT/EP2021/065556
§ 371 (c)(1),
(2) Date: Dec. 5, 2022

(87) PCT Pub. No.: WO2021/250145
PCT Pub. Date: Dec. 16, 2021

(65) Prior Publication Data
US 2023/0173270 A1 Jun. 8, 2023

(30) Foreign Application Priority Data

Jun. 12, 2020 (EP) .................................... 20179602

(51) Int. Cl.
*A61N 1/36* (2006.01)
*A61B 5/055* (2006.01)

(52) U.S. Cl.
CPC .......... *A61N 1/36034* (2017.08); *A61B 5/055* (2013.01)

(58) Field of Classification Search
CPC ............................ A61B 5/055; A61N 1/36034
(Continued)

(56) References Cited

U.S. PATENT DOCUMENTS

| | | | |
|---|---|---|---|
| 4,919,139 A | 4/1990 | Brodard | |
| 5,497,773 A | 3/1996 | Kuhara et al. | |
(Continued)

FOREIGN PATENT DOCUMENTS

| | | |
|---|---|---|
| CN | 109731227 A | 5/2009 |
| JP | 2005074156 B2 | 4/2005 |

OTHER PUBLICATIONS

Faber "Stimulation Peripherer Nerven Durch Zeitlich Veranderliche Magnetfeldgradienten in der Magnetresonanztomographie" Radiologe, Sep. 1, 1998 p. 743-749 (no translation available).
(Continued)

*Primary Examiner* — Nadia A Mahmood

(57) ABSTRACT

This disclosure provides a device (10) for preparing a patient for examination in a medical magnetic resonance imaging environment. The device comprises: at least one stimulation unit (11), adapted to operate separately from a magnetic stimulation used in the medical magnetic resonance imaging environment, and to intentionally stimulate a nerve and/or a muscle of a peripheral body part of the patient by applying an electrical and/or magnetic stimulation different from the magnetic stimulation used in the medical magnetic resonance imaging environment and being a proxy thereof; and at least one data processing unit (12), adapted to control the at least one stimulation unit to apply the electrical and/or magnetic stimulation to which at least one patient stimulation threshold is assigned; means for using the stimulation for communicating with the patient.

12 Claims, 2 Drawing Sheets

(58) Field of Classification Search
USPC .......................................................... 607/48
See application file for complete search history.

(56)                         References Cited

U.S. PATENT DOCUMENTS

| | | | |
|---|---|---|---|
| 6,169,403 B1* | 1/2001 | Hebrank et al. | |
| 2001/0020120 A1* | 9/2001 | Brand ................... | A61B 5/055 |
| | | | 600/9 |
| 2006/0241718 A1 | 10/2006 | Tyler et al. | |
| 2007/0010737 A1 | 1/2007 | Harvey et al. | |
| 2011/0152665 A1 | 6/2011 | Lai | |
| 2017/0248664 A1 | 8/2017 | Schnetter et al. | |

OTHER PUBLICATIONS

Akbari et al "Safe MRI-Compatable Electrical Muscle Stimulation" Journal of Magnetic Resonance Imaging, vol. 44, No. 6, May 17, 2016.
International Search Report and Written Opinion from PCT/EP2021/065556 mailed Sep. 2, 2021.
https://en.wikipedia.org/wiki/Electrical_muscle_stimulation downloaded Nov. 29, 2022.
https://en.wikipedia.org/wiki/Transcranial_magnetic_stimulation downloaded Nov. 29, 2022.

* cited by examiner

1

MRI INDUCED NERVE STIMULATION AS MEANS FOR COMMUNICATION WITH PATIENT

CROSS REFERENCE TO RELATED APPLICATIONS

This application is a U.S. national phase application of International Application No. PCT/EP2021/065556 filed on Jun. 10, 2021, which claims the benefit of EP Application Serial No. 20179602.6 filed on Jun. 12, 2020 and is incorporated herein by reference.

FIELD OF THE INVENTION

The present invention relates to medical imaging, and in particular to a device for preparing a patient for examination in a medical magnetic resonance imaging environment, a medical imaging system, a computer-implemented method for preparing a patient for examination in a medical magnetic resonance imaging environment, and a computer program element.

BACKGROUND OF THE INVENTION

Interaction with patients, such as a communicative interaction, in medical magnetic resonance imaging environments is challenging in case of noise, and it may require the integration of communication means in the medical magnetic resonance imaging environment etc. The latter may be difficult, since in e.g. magnetic resonance imaging (MRI) environments electromagnetic interaction of such a device with the MRI system is to be avoided, requiring additional technical measures. Beyond this, interaction with patients may also be desired in Computer Tomography (CT) imaging, Positron Emission Tomography (PET) imaging, or digital X-ray Radiogrammetry (DXR) imaging.

Interaction with patients during medical imaging can be useful for, for example, identifying a sedation status of a patient, repositioning of a patient, calming down an anxious patient, giving instructions for a certain way of breathing, or any other kind of instruction or the like.

SUMMARY OF THE INVENTION

There may, therefore, be a need for improved means for interacting with a patient undergoing a medical imaging procedure. The object of the present invention is solved by the subject matter of the independent claims, wherein further embodiments are incorporated in the dependent claims.

According to a first aspect, there is provided a device for preparing a patient for examination in a medical magnetic resonance imaging environment. The device comprises:

at least one stimulation unit, adapted to operate separately from a magnetic stimulation used in the medical magnetic resonance imaging environment, and to intentionally stimulate a nerve and/or a muscle of a peripheral body part of the patient by applying an electrical and/or magnetic stimulation different from the magnetic stimulation used in the medical magnetic resonance imaging environment and being a proxy thereof, and at least one data processing unit, adapted to control the at least one stimulation unit to apply the electrical and/or magnetic stimulation to which at least one patient stimulation threshold is assigned.

In this way, a patient may be prepared and/or trained for, particularly tactile, interaction and/or communication with the magnetic stimulation used in the medical magnetic resonance imaging environment before, during and/or after the actual examination in the medical magnetic resonance imaging environment. By using the at least one stimulation unit as a proxy, an additional arrangement of a complete device for magnetic stimulation as used in the medical magnetic resonance imaging environment can be omitted, resulting in considerable technical and cost savings. Further, the preparation of the patient can be done separately to the actual medical imaging examination, so that the medical magnetic resonance imaging environment, e.g. a medical imaging system, does not have to be used for the preparation of the patient but only for its actual medical imaging examination. This increases the efficiency of the medical magnetic resonance imaging environment, since it can be used exclusively for the actual examination. From a functional perspective, the above device allows for, by providing the proxy stimulation, reproducing the later stimulation in the medical magnetic resonance imaging environment as similar as possible or identical in order to have a recognition effect with the patient.

As used herein, preparing the patient may also be understood as to train the patient, for example, to get to know a tactile interaction and/or communication, and/or to make the patient familiar with this type of tactile interaction which is not known generally. This preparation phase or training phase may be performed separately, e.g. in a separate room, to a separate time, etc., to the actual examination in the medical magnetic resonance imaging environment, wherein the actual examination may also be referred to as the imaging phase. It may also be performed in separate rooms, facilities, etc.

"Proxy stimulation" as used herein may be understood as generating a comparable, similar or at least nearly identical stimulation without having to use the actual magnetic stimulation used in the medical magnetic resonance imaging environment, with other but possibly also the same technical means. For better differentiation, the terms "proxy stimulation" and "actual stimulation", i.e. the stimulation used in the medical magnetic resonance imaging environment, may also be used herein. Therefore, in other words, the proxy stimulation may mimic the actual stimulation during imaging. The proxy stimulation and the actual stimulation have in common that the patient feels this as a localized tactile sensation, for example a tickling sensation or spontaneous slight muscle contraction localized for example at the arms, the chest, or the back. By inducing either a single or multiple tactile signals by the stimulation at one or more locations a series of interactions, instructions etc., can be realized.

The at least one proxy stimulation unit may comprise, for example, an electric pulse generator that is adapted to generate electrical impulses to be provided to the patient, e.g. by use of a patient interface, such as a set of electrodes etc., and/or an electric pulse generator that is connected to a magnetic coil adapted to generate a changing electric current within the magnetic coil which induces a magnetic field. Optionally, the at least one stimulation unit may be a portable device. It may, optionally, also be battery-operated, so that preparation of the patient may be performed independent of location.

The "actual stimulation" as used herein, may utilize the effect of peripheral nerve stimulation (PNS). This can be used beneficially in the medical magnetic resonance imaging environment, since the strong currents applied to the magnetic resonance gradient coils during a MRI imaging procedure are known to have this undesirable side effect of PNS, which excites sensorial and motor nerves in the patient. The patient feels this as a tickling sensation or spontaneous slight muscle contraction typically at e.g. the arms or the back. This effect is normally considered to be undesirable and is avoided if at all possible during an MRI scan. Standard MRI systems have three independent gradient coils X, Y, Z, and each coil consists of several coil parts connected in series so that all parts carry the same current are driven by one of the gradient coil amplifiers X,Y,Z. The PNS effect can be intentionally utilized to stimulate a patient during an MRI scan, where parts of an MRI image acquisition unit could be utilized and with modifications further beneficial effects could be provided. Alternatively or additionally, a dedicated magnetic stimulation device, usable to stimulate the patient, could be used as an add-on to normal scanning with CT, PET and DXR for example.

The following discussion centers on an MRI imaging environment, however, the device, system and method as described herein have wider utility in other medical magnetic resonance imaging environments such as CT, PET and DXR. Thus, a tactile interaction with the patient, where a tactile sensation in the patient is created, is provided that would otherwise not be practical without additional devices. This is especially the case in closed bore systems, such as MRI systems, as there is no direct access to the bore during the scanning procedure. This is also generally the case in an autonomous imaging environment, where a minimum of staff or no staff at all is present for direct human interaction with the patient.

In an MRI environment, it is possible to make use of the undesirable PNS side effect of MR imaging as a basis of introducing a tactile communication path to the patient in the scanner. Thus, instead of trying to reduce the amount of PNS felt by the patient, involving new MR scan sequences, which intentionally induces PNS in the patient in a controlled manner. Thus, in an MRI system, at least a part of the gradient coils used for MRI can be used for intentional magnetic stimulation. For this purpose, strong currents may be applied to the MR gradient coils to induce PNS such that the waveforms of these currents are interleaved with the waveforms of the scan sequence used for MRI. Details of the conditions for interleaving are known to persons skilled in MR sequence design and in part described in the embodiments below. The strong currents are used to excite sensorial and motor nerves in the patient in a predefined spatial and temporal manner. Temporal behavior may be governed by the waveforms of the injected currents. Spatial behavior may be governed by the selection of particular coils for example with three coils with three associated amplifiers being used to generate a triple gradient (x, y, and z). Note that even a particular part of the gradient coils can be used, and where a single coil and amplifier can generate a single gradient e.g. x, y or z. Thus, two coils with two amplifiers can be used to generate a double gradient e.g. (x, y), or (x, z), or (y, z). Consequently, as mentioned above, the patient feels this as a localized tactile sensation, for example a tickling sensation or spontaneous slight muscle contraction localized for example at the arms or the back. By inducing either single or multiple tactile signals at one or more location a series of interactions can be realized.

According to an embodiment, the at least one stimulation unit used as a proxy may have a structurally simpler design and/or, optionally, may be more cost-effective than the gradient coil system in an MRI system or the magnetic stimulation unit used in other medical magnetic resonance imaging environment. In other words, the at least one stimulation unit used as a proxy does not necessarily have to provide the same type or technique of stimulation as in the medical magnetic resonance imaging environment, if the patient can perceive at least a similarity between the stimulations. Thus, the patient can, prior to the actual medical imaging examination, be well-prepared and/or trained for the interaction used during the medical imaging examination, without having to provide the same complex technical equipment additionally for the preparation phase.

In an embodiment, the at least one stimulation unit is adapted to apply the electrical and/or magnetic stimulation by one or more of: transcutaneous electrical nerve stimulation (TENS), electrical muscle stimulation or electromyo-stimulation (EMS), and transcranial magnetic stimulation (TMS).

TENS may be broadly understood as the use of electric current produced by a device, i.e. the at least one stimulation unit, to stimulate the nerves. For this purpose, two or more skin electrodes may be used, which are to be positioned on the patient's skin. Typically, there are three different classes of nerves which can be stimulated, those that activate muscles, pain nerves and thermally sensitive nerves. These classes of nerves usually differ from each other in e.g. their fibre type, diameter (in μm), conduction velocity (in m/s), and/or duration of action peak (in ms), wherein the at least one stimulation unit is controllable to provide different stimuli dependent on the classes of types and/or the desired sensation to be perceived by the patient. For example, the at least one stimulation unit may be adapted to provide one or more of the following TENS techniques having selectable parameters, such as a pulse rate and a pulse width: a conventional TENS, where a low intensity pulse of e.g. 60 to 200 Hz is applied continuously, a burst or AL-TENS, where a high intensity pulse of about 1000 Hz is applied in intervals, an intense TENS, where a high intensity pulse of about 200 Hz is applied continuously, a micro-current TENS, where an extremely low intensity pulse of about 200 Hz is applied continuously, an interferential TENS, where two or more different frequencies are crossed.

From a functional perspective, the proxy stimulation may be chosen to apply with the desired tactile sensation that mimics the actual stimulation as applied later in the medical magnetic resonance imaging environment, particularly during the imaging phase. Further, the type and/or number of electrodes may be chosen dependent on the desired mimic or tactile sensation and/or the stimulus to be applied. The stimulus may be chosen so as to reproduce the later stimulus in the medical magnetic resonance imaging environment as similar or identical as possible in order to have a recognition effect with the patient.

EMS may be broadly understood as an elicitation of muscle contraction using electric impulses. The at least one stimulation unit may be adapted to generate these electric impulses to be delivered through e.g. electrodes applied to the patient's skin near to the muscle being stimulated. Basically, the impulses mimic an action potential typically generated by the central nervous system, causing the muscle to contract.

TMS may be broadly understood as a noninvasive brain stimulation, where a changing magnetic field is used to cause electric current at a specific area of the brain through electromagnetic induction. For this purpose, the at least one stimulation unit may comprise an electric pulse generator that is connected to a magnetic coil, which is to be applied to the patient's scalp during operation. The at least one stimulation unit is adapted to generate a changing electric current within the coil which induces a magnetic field, wherein this field then causes a second inductance of inverted electric charge within the brain itself This allows an efficient preparation or training of the patient with technically simple means, without having to use the actual stimulation used in the medical magnetic resonance imaging environment.

According to an embodiment, the proxy stimulation provided by the at least one stimulation unit may be used for tactile communication with the patient, and the magnetic stimulation, i.e. the actual stimulation, used in the medical magnetic resonance imaging environment is adapted to provide a tactile communication that is at least similar to that of the at least one stimulation unit.

In other words, the intentional stimulation provided by the at least one stimulation unit is the proxy of the actual intentional magnetic stimulation, wherein the proxy stimulation mimics the actual stimulation.

This allows an efficient preparation or training of the patient with technically simple means.

In an embodiment the at least one data processing unit is adapted to control the at least one stimulation unit to apply the electrical and/or magnetic stimulation above the assigned at least one patient stimulation threshold.

This ensures that the patient perceives the stimulation properly. Preferably the electrical and/or magnetic stimulation is stimulated just above the assigned at least one patient stimulation threshold. With the term 'just above' is meant preferably less than 10% above the threshold, more preferably less than 5% above the threshold, even more preferably less than 2% above the threshold and most preferably less than 1% above the threshold. The closer the stimulation amount is above the threshold, the less likely the patient is affected negatively by the electrical and/or magnetic stimulation, which may be perceived as unpleasant at high amounts.

In an embodiment, the at least one data processing unit may further be adapted to provide, via an user interface, tactile interaction information data and/or tactile interaction instruction data associated with the proxy intentional stimulation to train the patient for tactile communication that is based on an intentional stimulation during the examination phase in the medical magnetic resonance imaging environment.

For example, the device may further comprise the user interface, such as an audio-interface and/or visual-interface, comprising e.g. a loudspeaker, headphone or the like, a display, or the like, adapted to provide the above data to the patient. The tactile interaction information data and/or tactile interaction instruction data may comprise, for example, an introduction to the concept of tactile interaction by using PNS, instructions to apply and/or reposition e.g. electrodes to the skin, an explanation of the stimulation currently applied, etc.

By way of example, the associated proxy intentional stimulation may be applicable a single or multiple times to the same or different parts of the patient's body, so as to indicate certain types of information. This information may also be content of tactile interaction information data and/or tactile interaction instruction data, so that the patient can recognize or train the tactile interaction in this context.

This allows the training to be more efficient and patient-friendly by providing appropriate instructions. Further, it allows a high degree of automation in medical imaging.

According to an embodiment, the at least one data processing unit may further be adapted to correlate the at least one patient stimulation threshold associated with the proxy electrical and/or magnetic stimulation with a corresponding threshold assigned to the magnetic stimulation used in the medical magnetic resonance imaging environment, and to provide, based on the correlation, a control parameter for applying the magnetic stimulation.

For example, a lookup table, a database, or the like may be provided, comprising thresholds for the actual stimulation and the proxy stimulation considering at least a given gradient coil and scan sequence and, optionally, e.g. a given set of skin electrode locations. These data may, for example, be collected in a test cohort of volunteers or patients. The at least one data processing unit may be adapted to access the threshold data and to determine the correlation. The determination may be based on the threshold of the proxy stimulation, which may be determined during the preparation phase.

This allows a direct setting of the actual stimulation only on the basis of the previous preparation phase.

In an embodiment, the at least one data processing unit may further be adapted to control the at least one stimulation unit to gradually increase a control parameter towards the at least one patient stimulation threshold, and to receive patient feedback on whether or not the stimulation is perceived by the patient, and to determine the patient stimulation threshold based on the patient's perception.

For example, the control parameter may be a voltage, a current, etc. with which the at least one stimulation unit is controlled. This control parameter may be gradually increased unit the patient can perceive or feel the stimulation, and so the threshold can be determined as at least the minimum value at which the patient perceives the stimulation. The patient feedback may be manually or electronically captured. Optionally, the device may further comprise means to receive the patient's feedback electronically, such as a data interface. The patient may use, for example, a manually operated signal generator to give the feedback to be received from the device. Optionally, the feedback may be captured automatically by a detection unit, such as a camera or the like, whose images may be evaluated by e.g. the device by e.g. image recognition techniques to determine the patient's feedback. Alternatively or additionally, the perception of the patient may be determined and/or measured by a sensor, such as a skin conductance (GSR) sensor, an EMG-sensor, a motion sensor, or the like.

Thus, the patient stimulation threshold can be determined accurately, and can be used for correlation with the threshold used for stimulation in the medical magnetic resonance imaging environment.

According to an embodiment, the at least one data processing unit may further be adapted to apply the proxy electrical and/or magnetic stimulation at a rate corresponding to a breathing rate desired for the patient during the examination in the medical magnetic resonance imaging environment.

For example, the proxy stimulation may be applied to a certain body part, such as the chest, in a periodic manner that matches the desired breathing rate for the medical imaging. The patient may be instructed to adapt his breathing rate to the proxy stimulation.

In an embodiment, the at least one data processing unit may further be adapted to vary an intensity of the proxy electrical and/or magnetic stimulation, when it is determined that the patient that the breathing rate is no longer within a desired range.

For example, the at least one data processing unit may vary a control parameter, such as a control voltage or a control current, This allows to instruct the patient to again keep the desired breathing rate.

According to an embodiment, at least one patient interface, arranged between the at least one proxy stimulation unit and the patient and adapted to apply the electrical and/or magnetic stimulation to the patient, the patient interface formed as one or more of a skin contact interface, a transmitter, and an emitter.

For example, the patient interface may comprise a set of electrodes, adapted to be applied to the patient's skin and to apply the proxy stimulation to the patient by skin contact. Further, the transmitter and/or the emitter may comprise at least one magnetic coil, adapted to generate a changing electric current within the magnetic coil which induces a magnetic field.

In an embodiment, the at least one data processing unit may further be adapted to determine, based on a measurement of one or more electric values, an indicator for positioning the at least one patient interface relative to or at the patient.

For example, the measurement may comprise a measurement of an electrical resistance between an electrode pair. Thereby, the lowest resistance path may be determined between the two specific electrodes. Such a low resistance path ensures that at last these two electrodes are positioned to activate a nerve—as the nerves are known to have a lower electrical resistance than the surrounding tissue.

This allows to increase the reliability of the stimulation threshold determination.

According to an embodiment, the patient interface may comprise at least one set of electrodes, connectable or connected to the at least one stimulation device and adapted to provide the electrical stimulation to the patient by contact. In an embodiment, the patient interface comprises at least one magnetic coil, connectable or connected to the at least one stimulation device and adapted to provide the magnetic stimulation to the patient by being applied tangentially to the patient's skull.

According to a second aspect, there is provided a medical imaging system. The system comprises:

a first device, the first device comprising:

at least one proxy stimulation unit, adapted to operate separately from a magnetic stimulation used in the medical magnetic resonance imaging environment, and to intentionally stimulate a nerve and/or a muscle of a peripheral body part of the patient by applying an electrical and/or magnetic proxy stimulation different from the magnetic stimulation used in the medical magnetic resonance imaging environment and being a proxy thereof, at least one first data processing unit, adapted to control the at least one proxy stimulation unit to apply the electrical and/or magnetic stimulation to which at least one patient stimulation threshold is assigned; and a second device, applied to the medical magnetic resonance imaging environment, the second device comprising:

a magnetic stimulation unit; and at least one second data processing unit, adapted to control the magnetic stimulation unit to intentionally stimulate a nerve and/or a muscle of a peripheral body part of the patient by applying a magnetic stimulation different from the proxy stimulation to a peripheral body part of the patient.

In this way, the patient can be trained by using the proxy stimulation to get known to or familiar with the actual stimulation, i.e. the magnetic stimulation, applied by the second device. By using the at least one stimulation unit as a proxy, an additional arrangement of a complete device for magnetic stimulation as used in the medical magnetic resonance imaging environment can be omitted, resulting in considerable technical and cost savings. Further, the preparation of the patient can be done separately to the actual medical imaging examination, so that the medical magnetic resonance imaging environment, e.g. a medical imaging system, does not have to be used for the preparation of the patient but only for its actual medical imaging examination. This increases the efficiency of the medical magnetic resonance imaging environment, since it can be used exclusively for the actual examination. From a functional perspective, the above device allows for, by providing the proxy stimulation, reproducing the later stimulation in the medical magnetic resonance imaging environment as similar or identical as possible in order to have a recognition effect with the patient.

For example, the first device may be configured as the device according to the first aspect as described above.

The second device may comprise at least one magnetic coil. The first and/or second data processing unit may be configured to control the at least one magnetic coil to provide the actual nerve and/or muscle stimulation to the patient in a predefined spatial and/or temporal manner.

In an embodiment, the first and/or second processing unit is configured to select at least one part of one magnetic stimulation coil of the at least one magnetic stimulation coil to provide the intentional nerve and/or muscle stimulation to the patient in the predefined spatial manner.

In an embodiment, the at least one magnetic coil may comprise a plurality of magnetic coils. The first and/or second processing unit may be configured to select at least a part of one or more magnetic stimulation coils of the plurality of magnetic stimulation coils to provide the intentional nerve and/or muscle stimulation to the patient in the predefined spatial manner.

In an embodiment, the first and/or second data processing unit may be adapted to control the magnetic stimulation unit to provide intentional nerve and/or muscle stimulation to a plurality of different locations of the patient.

In an embodiment, the first and/or second data processing unit may be adapted to control a waveform of a current applied to the at least one magnetic stimulation coil to provide the intentional nerve and/or muscle stimulation to the patient in the predefined temporal manner.

In an embodiment, the second device may comprise a plurality of magnetic stimulation coil drive amplifiers, and the at least one magnetic coil comprises a plurality of magnetic stimulation coils. Each magnetic coil is configured to be driven by at least one amplifier, wherein each amplifier is configured to drive only one magnetic coil, and wherein the processing unit is configured control the plurality of amplifiers to provide the intentional nerve and/or muscle stimulation to the patient in the predefined spatial and/or temporal manner.

In an embodiment, a first magnetic stimulation coil is configured to be driven by a first amplifier and a second magnetic stimulation coil is configured to be driven by a second amplifier. In an example, a third magnetic stimulation coil is configured to be driven by a third amplifier.

In this way, one coil can be driven by an amplifier to provide a single gradient (e.g. an x-gradient). However, when one coil is driven by one amplifier and a second coil is driven by a second amplifier two independent gradients can be generated (e.g. x, y). And, when a third coil is driven by a third amplifier a third independent gradient can be generated (x, y, z). It is to be noted that the amplifiers can provide independent magnetic stimulation fields (x, y, z) that need not be gradients as such.

In an embodiment, the first and/or second data processing unit may be configured to control the magnetic stimulation unit to provide intentional nerve and/or muscle stimuli to the patient to provide information to the patient.

In an embodiment, the second device may be configured to acquire at least one patient response to the nerve and/or muscle stimulations.

According to an embodiment, the magnetic stimulation unit may be controlled based on at least one patient stimulation threshold of the at least one stimulation unit.

As described above with respect to the first aspect, there may be performed a correlation and/or translation between the thresholds of the proxy stimulation provided by the at least one stimulation unit and that of the magnetic stimulation unit.

In further embodiments the device includes a controller for controlling the magnetic stimulation unit.

In an embodiment, the magnetic stimulation unit may be controlled, based on the at least one patient stimulation threshold, to perform a calibration scan, and patient feedback is received on whether or not the magnetic stimulation of the magnetic stimulation unit is perceived by the patient.

For example, the calibration scan may be initiated when the patient is already located in the medical magnetic resonance imaging environment, e.g. in a bore, however, before the actual imaging phase, e.g. an actual scanning sequence, is initiated to confirm that the threshold that has been determined during the preparation phase is indeed effective for interaction purposes, i.e. is perceive for the patient.

Optionally, in case of prior medical imaging procedures of a specific patient, a patient specific calibration file may be retrieved from a patient profile that was updated with the translation parameters (from the proxy stimulation to the actual stimulation).

According to an embodiment, the first device and the second device may be operatively connected to each other, and the magnetic stimulation unit is controlled based on monitoring data collected during the preparation phase.

The monitoring data may comprise, for example, observations on how good the patient can execute the specific interactions. Based on the observations, it may be determined, for example, whether an increased intensity level of the stimulation or the faster sequence or the increasing number of stimuli can support the imaging sequence to plan an optimized imaging sequence. improve interaction with the patient. Optionally, the monitoring data provided from the proxy stimulation device to the medical imaging system may indicate where the patient might have issues to detect or recognize the stimulation, which indication may be used to increase the stimulation during the actual medical imaging, i.e. the medical imaging phase. Thus, a stop of the medical imaging phase can be avoided, and thus enables the medical imaging procedure to be more efficient.

According to a third aspect, there is provided a computer-implemented method for preparing a patient for examination in a medical magnetic resonance imaging environment. The method comprises the steps of:

intentionally stimulating, during a preparation phase of the patient preceding an examination phase performed in the medical magnetic resonance imaging environment, a nerve and/or a muscle of a peripheral body part of the patient by applying an electrical and/or magnetic effect different from a magnetic stimulation used in the medical magnetic resonance imaging environment as a proxy thereof, and intentionally stimulating, during the examination phase performed in the medical magnetic resonance imaging environment, a nerve and/or a muscle of a peripheral body part of the patient by applying proxy magnetic stimulation to a peripheral body part of the patient.

The method may preferably be performed by use of the device according to the first aspect and/or by use of the system according to the second aspect.

According to a fourth aspect, there is provided a computer program element, which when executed by a processor is configured to carry out the method of the third aspect, and/or to control a system according to the second aspect, and/or to control a device according to the first aspect.

According to a fifth aspect, there is provided a computer-readable storage or transmission medium, which has stored or which carries the computer program element according to the fourth aspect.

It is noted that the above embodiments may be combined with each other irrespective of the aspect involved. Accordingly, the method may be combined with structural features of the device and/or system of the other aspects and, likewise, the device and the system may be combined with features of each other, and may also be combined with features described above with regard to the method.

These and other aspects of the present invention will become apparent from and elucidated with reference to the embodiments described hereinafter.

BRIEF DESCRIPTION OF THE DRAWINGS

Exemplary embodiments of the invention will be described in the following drawings.

DETAILED DESCRIPTION OF EMBODIMENTS

Figure 1:
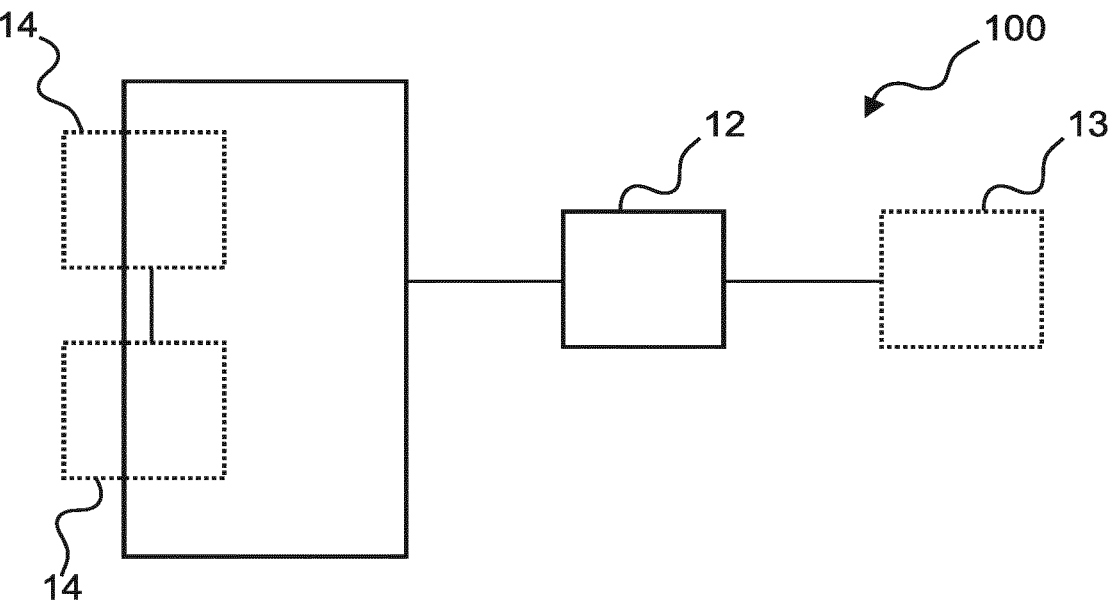
FIG. 1 shows in a schematic block diagram a device for preparing a patient for examination in a medical magnetic resonance imaging environment according to an embodiment.

FIG. 1 shows in a schematic block diagram a device 10 for preparing a patient for examination, i.e. a medical imaging procedure, that is performed in a medical magnetic resonance imaging environment according to an embodiment.

For this description, the medical magnetic resonance imaging environment can be differentiated from a preparation environment, wherein both environments are at least functionally and possibly also physically separated from each other, e.g. accommodated in separate rooms and/or facilities. The preparation environment is used to perform a preparation phase preceding an imaging phase performed in the imaging part.

The device 10 as described herein is dedicatedly applied to the preparation phase or the preparation environment, respectively. It serves as a proxy for at least one functional and/or structural part of the medical magnetic resonance imaging environment, as will be described in more detail below.

The device 10 comprises at least one stimulation unit 11, hereinafter referred to as proxy stimulation unit 11. The proxy stimulation unit 11 is adapted to operate separately from a magnetic stimulation, hereinafter referred to as the actual stimulation, applied in the medical magnetic resonance imaging environment during the imaging phase. The proxy stimulation unit 11 is adapted to intentionally stimulate a nerve and/or a muscle of a peripheral body part of the patient by applying an electrical and/or magnetic stimulation, hereinafter referred to as the proxy stimulation, different from the magnetic stimulation applied in the medical magnetic resonance imaging environment and being a proxy thereof. For this purpose, the proxy stimulation unit 11 comprises, for example, an electric pulse generator that is adapted to generate electrical impulses to be provided to the patient, e.g. by use of a patient interface, such as a set of electrodes etc. Alternatively or additionally, the proxy stimulation unit 11 comprises, for example, an electric pulse generator that is connected to a magnetic coil adapted to generate a changing electric current within the magnetic coil which induces a magnetic field.

The proxy stimulation unit 11 and/or the electric pulse generator comprised therefrom is adapted to apply the electrical and/or magnetic stimulation by one or more of: transcutaneous electrical nerve stimulation (TENS), electrical muscle stimulation (EMS), and transcranial magnetic stimulation (TMS).

Further, the device 10 comprises at least one data processing unit 12, which is adapted to control the at least one stimulation unit to apply the electrical and/or magnetic stimulation to which at least one patient stimulation threshold is assigned. The data processing unit 12 is, for example, a microprocessor or the like, and comprises one or more of a processor, a memory, a data interface, a communication interface, or the like.

Optionally, the device 10 may be a portable device, and may, optionally, be battery-operated.

From a functional perspective, the proxy stimulation provided by the proxy stimulation unit 11 may be used for tactile communication and/or interaction with the patient, and the magnetic stimulation applied in the medical magnetic resonance imaging environment is adapted to provide a tactile communication and/or interaction that is at least similar to that of the proxy stimulation unit, so that the patient can recognize an at least similar stimulation for both the preparation phase and the imaging phase.

Optionally, the data processing unit 12 may further be adapted to provide, via an user interface 13, tactile interaction information data and/or tactile interaction instruction data associated with the proxy intentional stimulation to train the patient for tactile communication that is based on an intentional stimulation during the examination phase in the medical magnetic resonance imaging environment. For example, the user interface 13 may comprise one or more of: an audio interface, such as a loudspeaker, headphone, or the like, to provide audio instructions to the patient, a visual interface, such as a display, a video screen, or the like, to provide visual instructions to the patient. For example, the tactile interaction information data and/or tactile interaction instruction data may be used to instruct or inform the patient on the different proxy stimulations that may be applied to the patient during the preparation phase, and/or on the meaning of the instruction, in order to train the patient to recognize a specific proxy stimulation that is assigned to a specific instruction.

Optionally, the data processing unit 12 may further be adapted to correlate the at least one patient stimulation threshold, i.e. first patient stimulation threshold, associated with the electrical and/or magnetic proxy stimulation with a corresponding threshold, i.e. second patient stimulation threshold, assigned to the magnetic stimulation used in the medical magnetic resonance imaging environment, and to provide, based on the correlation, a control parameter for applying the magnetic stimulation. For example, the control parameter may comprise a control voltage, a control current, etc.

Optionally, the data processing unit 12 may further be adapted to control the at least one stimulation unit 11 to gradually increase a control parameter towards the at least one patient stimulation threshold, and to receive patient feedback on whether or not the stimulation is perceived by the patient, and to determine the patient stimulation threshold based on the patient's perception. For example, the control parameter, e.g. the control voltage, can be gradually increased until the patient perceives the stimulation effect. This control parameter can then be set as the patient stimulation threshold, with optional extra margin.

Optionally, the data processing unit 12 may further be adapted to apply the electrical and/or magnetic proxy stimulation at a rate corresponding to a breathing rate desired for the patient during the examination in the medical magnetic resonance imaging environment.

Optionally, the device 10 comprises at least one patient interface 14, operatively and/or functionally arranged between the proxy stimulation unit 11 and the patient and adapted to apply the electrical and/or magnetic stimulation to the patient. The patient interface 14 may be formed as one or more of a skin contact interface, a transmitter, and an emitter. For example, the patient interface 14 may comprise a set of electrodes, adapted to be applied to the patient's skin and to apply the proxy stimulation to the patient by skin contact. Further, the transmitter and/or the emitter may comprise at least one magnetic coil, adapted to generate a changing electric current within the magnetic coil which induces a magnetic field.

Optionally, the data processing unit 12 may further be adapted to determine, based on a measurement of one or more electric values, an indicator for positioning the at least one patient interface relative to or at the patient. For example, the measurement may comprise a measurement of an electrical resistance between an electrode pair, used as the patient interface 14. Thereby, the lowest resistance path may be determined between the two specific electrodes. Such a low resistance path ensures that at last these two electrodes are positioned to activate a nerve—as the nerves are known to have a lower electrical resistance than the surrounding tissue.

Figure 2:
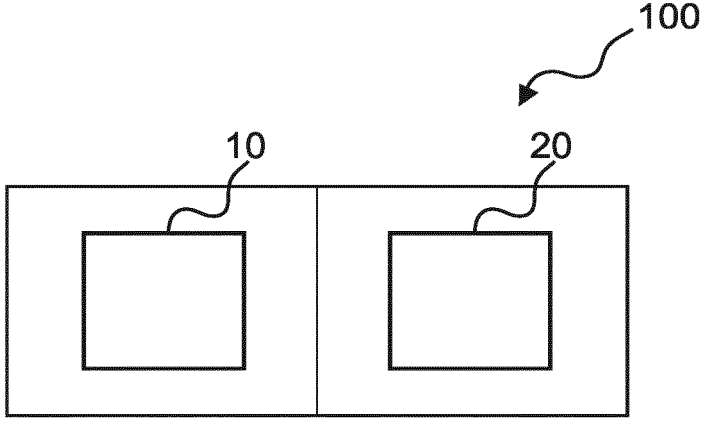
FIG. 2 shows in a schematic block diagram a medical imaging system according to an embodiment.

FIG. 2 shows a medical imaging system 100. For example, the medical imaging system 100 may be a Magnetic Resonance imaging (MRI) system; a Computer Tomography (CT) system, a Positron Emission Tomography (PET) system, a digital X-ray Radiogrammetry (DXR) system, or any other medical image system. It is noted that the medical imaging system comprises a suitable image acquisition unit suitable for performing the above techniques.

As described herein, the medical imaging system 100 comprises both the medical magnetic resonance imaging environment and the preparation environment.

Accordingly, the medical imaging system 100 comprises a first device, which may be formed as the device 10 as described above. Therefore, the device 10 comprises the at least one proxy stimulation unit 11, adapted to operate separately from a magnetic stimulation used in the medical magnetic resonance imaging environment, and to intentionally stimulate a nerve and/or a muscle of a peripheral body part of the patient by applying an electrical and/or magnetic proxy stimulation different from the magnetic stimulation used in the medical magnetic resonance imaging environment and being a proxy thereof. As described above, the device 10 further comprises the at least one first data processing unit 12, adapted to control the at least one proxy stimulation unit 11 to apply the electrical and/or magnetic stimulation to which at least one patient stimulation threshold is assigned.

The medical imaging system 100 further comprises a second device 20 of the medical magnetic resonance imaging environment. The second device 20 is dedicatedly applied to the preparation phase or the preparation environment 200, respectively. The second device 20 comprises at least one magnetic stimulation unit 21, and at least one second data processing unit 22, adapted to control the magnetic stimulation unit 11 to intentionally stimulate a nerve and/or a muscle of a peripheral body part of the patient by applying a magnetic stimulation different from the proxy stimulation to a peripheral body part of the patient.

Optionally, the magnetic stimulation unit 21 is controlled based on at least one patient stimulation threshold of the proxy stimulation unit 11.

Optionally, the magnetic stimulation unit 21 is controlled, based on the at least one patient stimulation threshold, to perform a calibration scan, and patient feedback is received on whether or not the magnetic stimulation of the magnetic stimulation unit 21 is perceived by the patient.

Optionally, the first device 10 and the second device 20 are operatively connected to each other, and the magnetic stimulation unit 21 is controlled based on monitoring data collected during the preparation phase.

Figure 3:
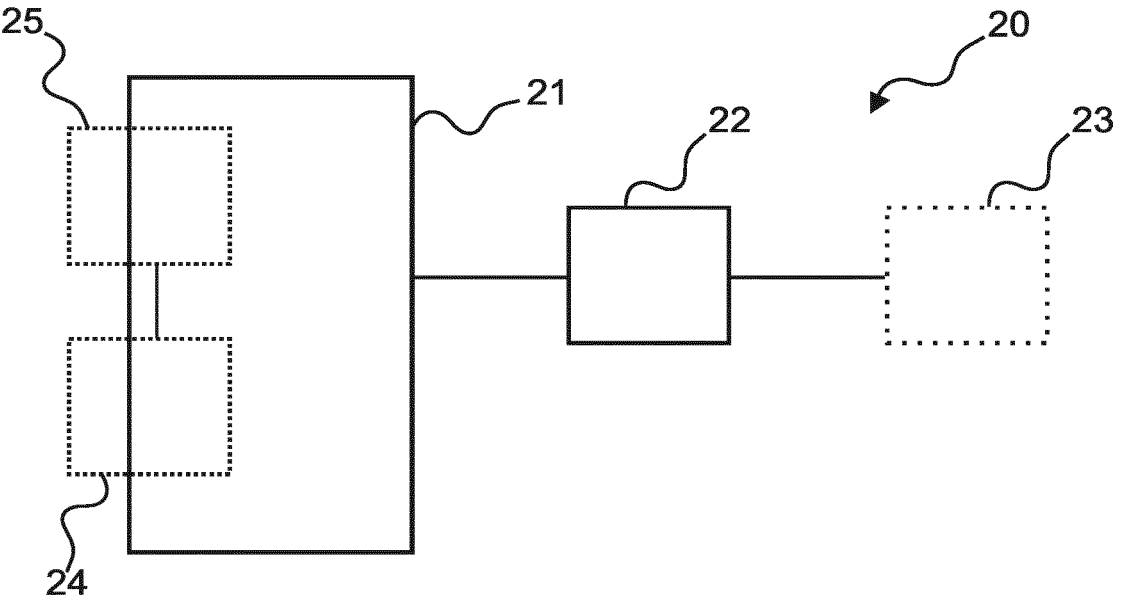
FIG. 3 shows in a schematic block diagram a device for providing magnetic stimulation to a patient according to an embodiment.

FIG. 3 shows in a schematic block diagram an example of the second device 20, comprising the magnetic stimulation unit 21, and the second data processing unit 22. The data processing unit 22 is configured to control the magnetic stimulation unit to provide intentional nerve and/or muscle stimulation to a peripheral body part of the patient.

Optionally, the second device 20 comprises at least one sensor device 23 configured to acquire at least one response to the nerve and/or muscle stimulation. For example, the at least one sensor device 23 comprises: a camera, an EMG sensor, a movement sensor, a tilt sensor, an accelerometer, a microphone, and the at least one sensor device can be the magnetic resonance image acquisition unit itself when operating in an image acquisition mode.

Optionally, the peripheral body part comprises a part of the leg, a part of the foot, a part of the arm, a part of the hand.

Optionally, the peripheral body part means any part of the body other than the head, and includes for example the back/spine.

Optionally, the second data processing unit 22 is configured to implement a specific instruction set to provide the intentional nerve and/or muscle stimuli to the patient.

Optionally, the second device 20 comprises at least one magnetic stimulation coil 24. The processing unit is configured to control the at least one magnetic stimulation coil to provide the intentional nerve and/or muscle stimuli to the patient in a predefined spatial and/or temporal manner.

Optionally, the at least one magnetic stimulation coil 24 is part of a magnetic resonance image acquisition unit.

Optionally, the at least one magnetic stimulation coil 424 comprises at least one gradient coil.

Optionally, the second data processing unit 22 is configured to select at least one part of one magnetic stimulation coil of the at least one magnetic stimulation coil 24 to provide the intentional nerve and/or muscle stimuli to the patient in the predefined spatial manner.

Optionally, the at least one magnetic stimulation coil 24 comprises a plurality of magnetic stimulation coils. The second data processing unit 22 is configured to select at least a part of one or more magnetic stimulation coils of the plurality of magnetic stimulation coils to provide the intentional nerve and/or muscle stimuli to the patient in the predefined spatial and/or temporal manner. Further optionally, the second device 20 comprises at least one or a plurality of magnetic stimulation coil drive amplifiers 25, and the at least one magnetic stimulation coil comprises a plurality of magnetic stimulation coils. Each magnetic stimulation coil is configured to be driven by at least one amplifier 25, wherein each amplifier 25 is configured to drive only one magnetic stimulation coil, and wherein the processing unit is configured control the plurality of amplifiers to provide the intentional nerve and/or muscle stimuli to the patient in the predefined spatial and/or temporal manner.

Optionally, the at least one magnetic stimulation coil is represented by at least one gradient coil of an MRI unit or system.

Optionally, reference to a magnetic stimulation coil can refer to a part of a gradient coil of an MRI unit or system.

Figure 4:
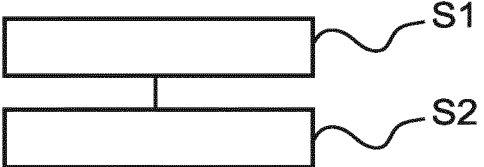
FIG. 4 shows a flow chart of a method for preparing a patient for examination in a medical magnetic resonance imaging environment according to an embodiment

With reference to FIG. 4, which shows a flow chart, a computer-implemented method for preparing a patient for examination in a medical magnetic resonance imaging environment will be described below.

In a step S1, an intentionally stimulating is performed, during a preparation phase of the patient preceding an examination phase performed in the medical magnetic resonance imaging environment, to a nerve and/or a muscle of a peripheral body part of the patient by applying an electrical and/or magnetic effect different from a magnetic stimulation used in the medical magnetic resonance imaging environment as a proxy thereof.

In a step S2, intentionally magnetic stimulating is performed, during the examination phase performed in the medical magnetic resonance imaging environment, to a nerve and/or a muscle of a peripheral body part of the patient by applying magnetic stimulation to a peripheral body part of the patient.

Note that the nerve and/or muscles of Steps S1 and S2 may comply with each other, or may be in a same region of the patient's body.

The following detailed embodiments provide further details on how the device 10, the medical imaging system 100, and the method for preparing the patient can be realised as would be appreciated by the skilled person.

Embodiment 1: Mimic PNS Interaction by Electromyostimulation During Audio-Visual
Introduction Patients typically enter a preparation area or room, where the preparation phase may be performed, before the actual examination, i.e. the imaging phase. Especially in an autonomous setting, there may be an extended patient preparation that already includes some audio-visual introduction to the next steps of the MR examination.

In at least some embodiments, the patient may be introduced to the concept of tactile interaction by utilizing PNS and to mimic it during this training using the electrical and/or magnetic stimulation provided by the proxy stimulation unit.

In at least some embodiments, direct galvanic electrical stimulation using skin electrodes as performed in EMS training devices for muscles may be used. For this purpose, the electrodes may temporarily be attached during the preparation phase, or may be integrated in a chair or patient support. Preferably, the electrodes are in the form of a patch. Such a patch is in the form of a matrix of electrodes. In operation, the electrical resistance between each of the electrode pairs may be measured and the lowest resistance path between two specific electrodes is determined. Such a low resistance path indicates that at last these two electrodes are optimally positioned to activate a nerve—as the nerves are known to have a lower electrical resistance than the surrounding tissue. Using this approach may also increase the reliability of the stimulation threshold determination, as described in embodiment 4 below.

Embodiment 2: Use of ECG-Electrodes

If the patient is prepared for cardiac-triggered scans in the medical magnetic resonance imaging environment, electrocardiogram (ECG) electrodes are typically applied to the chest of the patient for triggering and connected to an ECG receive amplifier system during the imaging phase, i.e. scanning. In at least some embodiments, these electrodes are already applied to the patient during the preparation phase, where the electronics are connected to the proxy stimulation unit 11, which may comprise a transmission amplifier that can deploy waveforms for providing the electrical stimulation, such as EMS.

Embodiment 3: Mimic PNS Interaction by Transcranial Magnetic Stimulation (TMS)

Transcranial magnetic stimulation (TMS) may be used to produce muscle activity or sensations similar to PNS by using magnetic coils applied to the skull, inducing activity in respective brain tissue of the cortex. TMS applied at the skull or on another part of the patient's body may be used to mimic PNS alternatively to EMS as described in embodiment 1 above.

Embodiment 4: Adaptation of Patient Stimulation Thresholds

The actual patient stimulation thresholds and the proxy patient stimulation thresholds may vary widely across patients. However, both types of patient stimulation thresholds are expected to be linked for a particular patient because both, the proxy stimulation and the actual stimulation are caused by electrical fields acting on motor and sensory nerves. The main difference between the actual stimulation and the proxy stimulation can be seen in that in the latter case the fields are induced without any galvanic contact but by rapidly changing magnetic fields.

In at least some embodiments, the data processing unit 12 is adapted, by e.g. a suitable computer program, to correlate the actual stimulation threshold and the proxy stimulation threshold for a given gradient coil in the medical magnetic resonance imaging environment and an given imaging scan sequence and, optionally, for a given set of electrode locations, which data may, for example, be derived from a test cohort of volunteers or patients.

Optionally, for a given patient, one or more individual proxy stimulation thresholds may be determined during the preparation phase by gradually increasing the applied control parameter, e.g. control voltages or currents, until the patient perceives, e.g. can feel, the proxy stimulation. The above correlation of the actual stimulation threshold and the proxy stimulation threshold may then be used to translate the determined proxy stimulation threshold into a suitable gradient current used in the PNS sequences applied for tactile interaction during the imaging phase in the medical magnetic resonance imaging environment.

Optionally, the proxy stimulation threshold determined as described above may be used to control a (single) PNS inducing scan in the medical magnetic resonance imaging environment. This scan, which may also be referred to as a calibration scan, may be initiated when the patient is in the medical magnetic resonance imaging environment, e.g. in a bore, but before the actual scanning sequence. i.e. the actual imaging phase, is initiated to confirm that the assessed threshold is indeed effective for interaction purposes.

In case of prior imaging procedures assigned to a specific patient, a patient specific calibration file may be retrieved from a patient profile that was updated with the translation parameters (from the proxy stimulation threshold to the actual stimulation threshold).

Optionally, a dedicated device to measure this translation parameter may be used for the preparation phase, where the device may be adapted to generate a magnetic field and the PNS sequence, wherein the device does not have to be a functional MRI scanner, but have a simpler structural design.

Embodiment 5: Training for Specific Purposes as Breathing Guidance

The patient may be trained so as to recognize the actual stimulation, i.e. PNS, applied a single or multiple times to the same or different parts of the body will indicate certain types of information.

By way of example, the patient may be trained that PNS is used to act as a stimulus to guide breathing during MR scanning without having to physically touch the patient or address him per audio commands. Preferably, the proxy stimulation training may be applied multiple times to the chest of the patient in a periodic manner with the desired breathing rate of the patient. Further optionally, an intensity of the proxy stimulation can be altered to indicate to patients that they do no longer comply with breathing guidance properly.

Observations how good the patient may execute the specific sequences and how the patient react on the altered intensity of the proxy stimulation may provide information on whether the faster sequence or increasing number of stimuli support the imaging sequence can be used to plan for the optimized imaging sequence. The communication from the proxy device to the actual medical imaging system may also indicate where the patient might have issues to detect or recognize the stimulus which enables to retrigger the stimulation during the imaging sequence without stopping which makes the complete process more efficient.

The complete workflow as described herein, including patient profiling and setting the correct system parameters per patient type, may be optimized via artificial intelligence, AI, learning algorithms to identify and estimate the success rate and also to identify which group of patients will probably have problems with the applied method. These patients then could directly be supported by other methods and supporting staff which overall leads to a more efficient process.

Embodiment 6: Improve Calibration and Communication Via PNS in the Medical Magnetic Resonance Imaging Environment After the preparation or training phase the patient is moved to the medical magnetic resonance imaging environment, e.g. the medical imaging system, and a calibration scan may be performed. The proxy stimulation during the preparation or training phase may, in some cases, not well represent the actual stimulation induced in the medical magnetic resonance imaging environment, since individual actual stimulation, i.e. the PNS communication signal, depends on the individual shape of the human body. The calibration scan allows the patient to adapt to the actual stimulation, i.e. the real situation. Optionally, the calibration scan may be supported using a vital signs signal (e.g. an RF Pilot tone, RADAR, US, or VitalEye infrastructure). Indicator of PNS are motion in correlation to gradient waveform, sudden reaction of patient (eye, face, body). The vital signs signal contains all patient motion. The ones, that are due to PNS will correlate exactly with the MR scanner gradient induced PNS. Therefore, a correlation of the vital signs signal and the gradient time pattern will give a clear indication if PNS is happening. The signals can be represented by a further optical communication signal to the patient.

For calibration the medical imaging system may be adapted to send a few test gradient pulses prior to the scan, up to the strongest/fastest programmed gradient rise, in order to estimate if and when PNS will occur and the patient can accept if the calibration fits with the calculated parameters represented by the external stimulation.

During the calibration process, the combination of a PNS communication signal and visual or acoustic stimulation may further improve and optimize the process of training. For example, the PNS level may be shown visually so that patient can learn and adapt and react to even weak PNS signals. Using this additional information may further improve (by e.g. a feedback loop) the calibration of the PNS communication signal.

In another exemplary embodiment, a computer program or computer program element is provided that is characterized by being configured to execute the method steps of the method according to one of the preceding embodiments, on an appropriate system.

The computer program element might therefore be stored on a data processing unit, which might also be part of an embodiment. This data processing unit may be configured to perform or induce performing of the steps of the method described above. Moreover, it may be configured to operate the components of the above described device and/or system. The computing unit can be configured to operate automatically and/or to execute the orders of a user. A computer program may be loaded into a working memory of a data processor. The data processor may thus be equipped to carry out the method according to one of the preceding embodiments.

Further, the computer program element might be able to provide all necessary steps to fulfill the procedure of an exemplary embodiment of the method as described above.

According to a further exemplary embodiment of the present invention, a computer readable medium, such as a CD-ROM, USB stick or the like, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It is noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and the foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

LIST OF REFERENCE SIGNS

100 medical imaging system
10 device
11 stimulation unit
12 data processing unit
13 user interface
14 patient interface
20 device
21 magnetic stimulation unit
22 data processing unit
23 sensor device
24 magnetic stimulation coil
25 magnetic stimulation coil drive amplifier

The invention claimed is:

1. A system for preparing a patient for examination in a medical magnetic resonance imaging environment, comprising:

a magnetic resonance imaging unit, applied to the medical magnetic resonance imaging environment during an examination phase and comprising at least one magnetic coil controlled to provide magnetic stimulation to intentionally stimulate a nerve and/or muscle of a peripheral body part of the patient;

a first device, applied in a preparation phase of the patient preceding the examination phase;

wherein the magnetic resonance imaging unit and the first device are configured to provide tactile communication with the patient by intentionally stimulating a nerve and/or muscle of a peripheral body part of the patient;

wherein the first device comprises:

at least one stimulation unit, adapted to be a proxy of the magnetic resonance imaging unit by mimicking a later magnetic stimulation of the magnetic resonance imaging unit as a proxy electrical and/or magnetic stimulation and to operate separately from the magnetic stimulation from the medical magnetic resonance imaging unit, and to intentionally stimulate a nerve and/or a muscle of a peripheral body part of the patient by applying an electrical and/or magnetic stimulation by means different from the magnetic stimulation of the magnetic resonance imaging unit and at least one data processing unit, adapted to control the at least one stimulation unit to apply the electrical and/or magnetic stimulation, wherein at least one patient stimulation threshold is assigned to the proxy electrical and/or magnetic stimulation; and the at least one data processing unit is further adapted to correlate the at least one patient stimulation threshold associated with the proxy electrical and/or magnetic stimulation with a corresponding threshold assigned to the magnetic stimulation used in the medical magnetic resonance imaging environment, and to provide, based on the correlation, a control parameter for applying the later magnetic stimulation of the magnetic resonance imaging unit;

wherein the at least one data processing unit is further adapted to provide, via a user interface, tactile interaction information data and/or tactile interaction instruction data associated with the proxy electrical and/or magnetic stimulation to train the patient for tactile communication during the later magnetic examination.

2. Thee system according to claim 1, wherein the at least one stimulation unit is adapted to apply the electrical and/or magnetic stimulation by one or more of:

transcutaneous electrical nerve stimulation, TENS, electrical muscle stimulation, EMS, and transcranial magnetic stimulation, TMS.

3. The system according to claim 1, wherein the at least one data processing unit, adapted to control the at least one stimulation unit to apply the electrical and/or magnetic stimulation above the assigned at least one patient stimulation threshold.

4. The system according to claim 1, wherein the at least one data processing unit is further adapted to control the at least one stimulation unit to gradually increase a control parameter towards the at least one patient stimulation threshold, and to receive patient feedback on whether or not the stimulation is perceived by the patient, and to determine the patient stimulation threshold based on a perception of the patient.

5. The system according to claim 1, wherein the at least one data processing unit is further adapted to apply the proxy electrical and/or magnetic stimulation at a rate corresponding to a breathing rate desired for the patient during the examination in the medical magnetic resonance imaging environment.

6. The system according to claim 1, further comprising:

at least one patient interface, arranged between the at least one stimulation unit and the patient and adapted to apply the electrical and/or magnetic stimulation to the patient, the patient interface formed as one or more of a skin contact interface, a transmitter, and an emitter.

7. The system according to claim 6, wherein the at least one data processing unit is further adapted to determine, based on a measurement of one or more electric values, an indicator for positioning the at least one patient interface relative to or at the patient.

8. The system according to claim 1, further comprising:

a controller that is adapted to control the at least one magnetic coil based on at least one patient stimulation threshold of the at least one stimulation unit.

9. The system according to claim 8, wherein the controller is further adapted to control the at least one stimulation unit, based on the at least one patient stimulation threshold, to perform a calibration scan, and patient feedback is received on whether or not the electrical and/or magnetic stimulation of the at least one stimulation unit is perceived by the patient.

10. The system according to claim 1, wherein the first device and a second device are operatively connected to each other, and the controller is adapted to control the at least one stimulation unit based on monitoring data collected during the preparation phase.

11. A method for tactile communication with a patient in a medical magnetic resonance imaging environment, wherein the method is applied to a system comprising a magnetic resonance imaging unit, applied during an examination phase, and at least one stimulation unit, applied to a preparation phase preceding the examination phase, wherein the magnetic resonance imaging unit and the at least one stimulation unit are configured to provide the tactile communication with the patient by intentionally stimulating a nerve and/or muscle of a peripheral body part of the patient, and wherein the method comprises:

causing the at least one stimulation unit which is a proxy of the magnetic resonance imaging unit by mimicking a later magnetic stimulation of the magnetic resonance imaging unit as a proxy electrical and/or magnetic stimulation and operates separately from the magnetic stimulation of the magnetic resonance imaging unit to intentionally stimulate, a nerve and/or a muscle of a peripheral body part of the patient by applying an electrical and/or magnetic effect different from a magnetic stimulation of the magnetic resonance imaging unit, and controlling the magnetic resonance imaging unit to intentionally stimulate, during the examination phase, a nerve and/or a muscle of a peripheral body part of the patient by applying the magnetic stimulation different from the proxy electrical and/or magnetic stimulation to a peripheral body part of the patient.

12. A computer program product, comprising executable instructions stored on a non-transitory computer readable medium which when executed by a processor, controls a device according to claim 1.

\*  \*  \*  \*  \*